(12) United States Patent  
Oberkampf et al.

(10) Patent No.: US 9,002,769 B2  
(45) Date of Patent: Apr. 7, 2015

(54) METHOD AND SYSTEM FOR SUPPORTING A CLINICAL DIAGNOSIS

(75) Inventors: Heiner Oberkampf, München (DE); Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 304 days.

(21) Appl. No.: 13/540,952

(22) Filed: Jul. 3, 2012

(65) Prior Publication Data

US 2014/0012790 A1    Jan. 9, 2014

(51) Int. Cl.
*G06N 5/02* (2006.01)
*G06F 19/00* (2011.01)

(52) U.S. Cl.
CPC .................................. *G06F 19/345* (2013.01)

(58) Field of Classification Search
None
See application file for complete search history.

(56) References Cited

U.S. PATENT DOCUMENTS

| | | | | |
|---|---|---|---|---|
| 5,822,743 A * | 10/1998 | Gupta et al. | ..................... | 706/50 |
| 6,246,975 B1 * | 6/2001 | Rivonelli et al. | ................ | 703/11 |
| 6,468,210 B1 * | 10/2002 | Iliff | .............................. | 600/300 |
| 6,475,143 B2 * | 11/2002 | Iliff | .............................. | 600/300 |
| 6,524,241 B2 * | 2/2003 | Iliff | .............................. | 600/300 |
| 6,527,713 B2 * | 3/2003 | Iliff | .............................. | 600/300 |
| 6,569,093 B2 * | 5/2003 | Iliff | .............................. | 600/300 |
| 6,730,027 B2 * | 5/2004 | Iliff | .............................. | 600/300 |
| 6,746,399 B2 * | 6/2004 | Iliff | .............................. | 600/300 |
| 6,764,447 B2 * | 7/2004 | Iliff | .............................. | 600/300 |
| 6,767,325 B2 * | 7/2004 | Iliff | .............................. | 600/300 |
| 6,817,980 B2 * | 11/2004 | Iliff | .............................. | 600/300 |
| 7,117,185 B1 * | 10/2006 | Aliferis et al. | ................... | 706/12 |
| 7,392,199 B2 * | 6/2008 | Karlov et al. | ...................... | 705/2 |
| 7,512,576 B1 * | 3/2009 | Syeda-Mahmood et al. | ... | 706/45 |
| 8,019,582 B2 * | 9/2011 | Iliff | .............................. | 703/11 |
| 8,068,993 B2 * | 11/2011 | Karlov et al. | ................... | 702/19 |
| 2001/0020229 A1 * | 9/2001 | Lash | ................................ | 705/3 |
| 2002/0002325 A1 * | 1/2002 | Iliff | .............................. | 600/300 |
| 2002/0013515 A1 * | 1/2002 | Iliff | .............................. | 600/300 |
| 2002/0016529 A1 * | 2/2002 | Iliff | .............................. | 600/300 |
| 2002/0040183 A1 * | 4/2002 | Iliff | .............................. | 600/300 |
| 2002/0052540 A1 * | 5/2002 | Iliff | .............................. | 600/300 |
| 2002/0068857 A1 * | 6/2002 | Iliff | .............................. | 600/300 |
| 2002/0161664 A1 * | 10/2002 | Shaya et al. | ..................... | 705/26 |
| 2003/0045782 A1 * | 3/2003 | Iliff | .............................. | 600/300 |
| 2003/0065535 A1 * | 4/2003 | Karlov et al. | ..................... | 705/2 |
| 2003/0073887 A1 * | 4/2003 | Iliff | .............................. | 600/300 |
| 2003/0144580 A1 * | 7/2003 | Iliff | .............................. | 600/300 |
| 2003/0158468 A1 * | 8/2003 | Iliff | .............................. | 600/300 |
| 2003/0199740 A1 * | 10/2003 | Iliff | .............................. | 600/300 |

(Continued)

*Primary Examiner* — Ben Rifkin
*Assistant Examiner* — Fuming Wu
(74) *Attorney, Agent, or Firm* — King & Spalding L.L.P.

(57) ABSTRACT

A method and system for supporting a clinical diagnosis is provided, the method including the steps of representing a patient by a plurality of initial symptoms, the symptoms including characteristics of the patient; determining, by querying and reasoning in a disease-symptom knowledge model, at least one likely disease for each of the plurality of initial symptoms; mapping the plurality of initial symptoms onto a set of said likely diseases; determining for each disease of said set of likely diseases a plurality of associated symptoms, the associated symptoms being associated to a respective disease of said set of likely diseases in said disease-symptom knowledge model; categorizing each of the plurality of associated symptoms into disjoint categories by mapping associated symptoms with initial symptoms; and representing likely diseases in the context of said categories of associated symptoms.

11 Claims, 2 Drawing Sheets

(56) References Cited

U.S. PATENT DOCUMENTS

| | | | |
|---|---|---|---|
| 2004/0122787 A1* | 6/2004 | Avinash et al. | 706/50 |
| 2004/0122790 A1* | 6/2004 | Walker et al. | 707/1 |
| 2004/0162835 A1* | 8/2004 | Ghouri | 707/100 |
| 2004/0199332 A1* | 10/2004 | Iliff | 702/19 |
| 2005/0031651 A1* | 2/2005 | Gervais et al. | 424/400 |
| 2006/0218010 A1* | 9/2006 | Michon et al. | 705/3 |
| 2009/0007924 A1* | 1/2009 | Iliff | 128/898 |
| 2009/0024332 A1* | 1/2009 | Karlov et al. | 702/19 |
| 2009/0042224 A1* | 2/2009 | Hellstrom et al. | 435/7.92 |
| 2009/0110745 A1* | 4/2009 | Shea et al. | 424/523 |
| 2009/0157663 A1* | 6/2009 | Kate | 707/5 |
| 2010/0211327 A1* | 8/2010 | Hahner et al. | 702/19 |
| 2011/0065204 A1* | 3/2011 | Wollert et al. | 436/501 |
| 2011/0098193 A1* | 4/2011 | Kingsmore et al. | 506/9 |
| 2011/0106821 A1* | 5/2011 | Hassanzadeh et al. | 707/749 |
| 2011/0144914 A1* | 6/2011 | Harrington et al. | 702/19 |
| 2011/0196007 A1* | 8/2011 | Honda et al. | 514/400 |
| 2011/0269143 A1* | 11/2011 | Thorlacius et al. | 435/6.14 |
| 2011/0307437 A1* | 12/2011 | Aliferis et al. | 706/52 |
| 2013/0268203 A1* | 10/2013 | Pyloth | 702/19 |
| 2013/0310653 A1* | 11/2013 | Zillner et al. | 600/300 |
| 2014/0012790 A1* | 1/2014 | Oberkampf et al. | 706/46 |
| 2014/0122380 A1* | 5/2014 | von Mueller et al. | 706/11 |
| 2014/0279721 A1* | 9/2014 | Siegel et al. | 706/11 |

* cited by examiner

METHOD AND SYSTEM FOR SUPPORTING A CLINICAL DIAGNOSIS

TECHNICAL FIELD

The disclosure provides a method and system for supporting a clinical diagnosis.

BACKGROUND

Current systems for supporting clinical diagnosis rely on an efficient management, linking as well as accessing of heterogeneous knowledge and data resources, such as personal patient records including data ranging from structured to unstructured data and from annotated medical images to lab results to dictated reports.

Although large amounts of clinical data is available, it is still difficult to automatically use and integrate the data within currently used clinical diagnose decision support systems.

This is mainly due to a lack of seamless integration of information and knowledge in current systems for supporting clinical diagnosis. In particular, the integration of knowledge and information requires the availability of semantic annotation of information entities on the respective level of detail in order to explicitly capture their content information as well as the interpretation of annotations, e.g. the significance of a particular observation in the context of likely diseases.

Although annotations are supported by most currently used systems an integration of annotated patient data within clinical decision support systems is still difficult to realize. This is due to the fact, that the corresponding annotations do only capture the descriptive information of its content, i.e. the observations made, the findings discovered, the various symptoms identified.

However, in clinical diagnosis decision systems, the descriptive data items need to be interpreted in the context of one particular or a set of likely diseases. For being able to automatically infer the relevance of symptoms and findings in the context of a particular disease, explicit information about relations between possible symptoms and possible diagnoses would be required.

Clinicians are usually experts in one particular domain, such that they often lack prior knowledge of how particular symptoms might relate to diseases that are out-of-scope of their expertise. In other words, there is the clear danger that the information about the relevance of identified symptoms remains overlooked or misinterpreted, leading to wrong or not appropriate treatments, etc.

SUMMARY

In one embodiment, a method for supporting a clinical diagnosis may include the steps of: a) representing a patient by a plurality of initial symptoms, the symptoms including characteristics of the patient; b) determining, by querying and reasoning in a disease-symptom knowledge model, at least one likely disease for each of the plurality of initial symptoms; c) mapping the plurality of initial symptoms onto a set of said likely diseases; d) determining for each disease of said set of likely diseases a plurality of associated symptoms, the associated symptoms being associated to a respective disease of said set of likely diseases in said disease-symptom knowledge model; e) categorizing each of the plurality of associated symptoms into disjoint categories by mapping associated symptoms with initial symptoms; and f) representing likely diseases in the context of said categories of associated symptoms.

In a further embodiment, in step e) symptoms are categorized in a category of: existing symptoms in case that a particular associated symptom is equally mapped by an initial symptom; absent symptoms in case that a particular associated symptom is explicitly excluded in the mapping of said plurality of initial symptoms; or open symptoms in case that a particular associated symptom is missing in the mapping of said plurality of initial symptoms. In a further embodiment, the method includes the step of g) enabling a user to change said categories of each of the plurality of associated symptoms. In a further embodiment, the method includes the step of h) enabling a user to request information entities stored in a record of the patient, the information entities being semantically related to at least one open symptom of said set of likely diseases. In a further embodiment, the method includes the step of i) inferring recommended examination steps by evaluating existing, absent and/or open symptoms in view of said disease-symptom knowledge model.

In a further embodiment, said initial symptoms include findings, observations, symptoms and/or negated symptoms. In a further embodiment, the method includes the step of treating the associated symptoms in step e) as initial symptoms and recurring the steps b) until f).

In another embodiment, a system for supporting a clinical diagnosis may comprise: a semantic patient data repository including semantically annotated initial symptoms representing a patient, the symptoms including characteristics of the patient; an ontology repository including a knowledge model establishing a relationship between a plurality of diseases and a plurality of associated symptoms; a query and reasoning component for mapping the plurality of initial symptoms onto a set of likely diseases and for mapping the plurality of initial symptoms onto a set of said likely diseases; a ranking module for categorizing each of the plurality of associated symptoms into disjoint categories by mapping associated symptoms with initial symptoms; and a user interaction module for representing likely diseases in the context of said categories of associated symptoms.

In yet another embodiment, a computer program product contains a program code stored on a computer-readable medium and which, when executed on a computer, carries out any of the methods disclosed above.

In still another embodiment, a data storage carrier stores a computer program to cause a computer to perform any of the methods disclosed above.

BRIEF DESCRIPTION OF THE DRAWINGS

Example embodiments will be explained in more detail below with reference to figures, in which.

DETAILED DESCRIPTION

Figure 1:
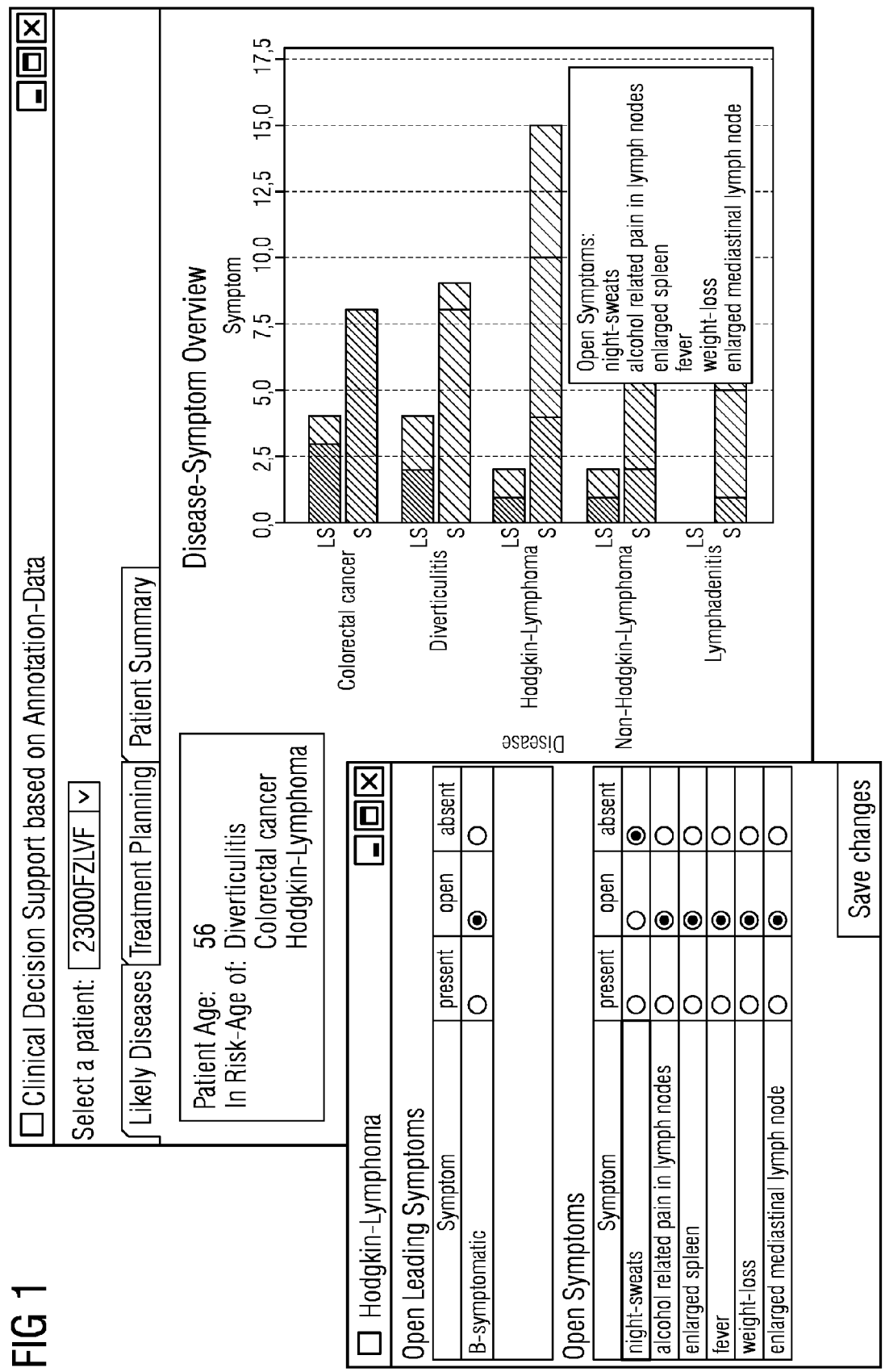
FIG. 1 shows an exemplary user interface for representing likely diseases in the context of said categories of associated symptoms.

Some embodiments provide methods and systems for evaluating clinical observations in the context of likely diseases, thereby supporting clinicians to improve their decisions in terms of further diagnosis and/or treatment of the patient.

According to an embodiment, a method for supporting a clinical diagnosis is provided, the method may include the steps of:

a) representing a patient by a plurality of initial symptoms, the symptoms including characteristics of the patient;

b) determining, by querying and reasoning in a disease-symptom knowledge model, at least one likely disease for each of the plurality of initial symptoms;

c) mapping the plurality of initial symptoms onto a set of said likely diseases;

d) determining for each disease of said set of likely diseases a plurality of associated symptoms, the associated symptoms being associated to a respective disease of said set of likely diseases in said disease-symptom knowledge model;

e) categorizing each of the plurality of associated symptoms into disjoint categories by mapping associated symptoms with initial symptoms;

f) representing likely diseases in the context of said categories of associated symptoms.

The proposed method may establish a mechanism for the seamless and interactive navigation and documentation of patient data by means of a formally captured disease-symptom knowledge model. The proposed method aims to support medical experts in the patient's diagnose process by representing the relevance of symptoms in the context of likely diseases.

Given a patient with an initial set of symptoms, said initial set of symptoms, e.g., available within patient's records, the proposed method is aiming to infer a representation of likely diseases in the context of associated symptoms of the patient.

The representation is exemplarily shown by a ranked list of likely diseases. From the disease-symptom knowledge model, e.g., an ontology, and the initial set of symptoms a list of likely diseases is derived. In a further step, for each likely disease a plurality of associated symptoms is determined.

The set of associated symptoms can be split into three categories for each disease:

existing symptoms for which corresponding annotations were found, or, in other words, for which a particular associated symptom of a likely disease is equally mapped by an initial symptom;

absent symptoms, e.g. symptoms researched by a medical inspection but did not show up (e.g. „no enlarged lymph nodes in neck area« . In other words absent symptoms are symptoms for which a particular associated symptom of a likely disease is explicitly excluded in the mapping of said plurality of initial symptoms; and open symptoms without any corresponding annotation data. These symptoms have not been examined yet and potentially need to be targeted next. In other words absent symptoms are symptoms for which a particular associated symptom of a likely disease is missing in the mapping of said plurality of initial symptoms.

According to one embodiment of the method, a user is enabled to change the categories of each of the plurality of associated symptoms. In the context of a particular patient, the information of likely disease and the associated classification of symptoms are represented to the clinician by means of an interaction mechanism that allows the clinician to change the patient's symptom categories. For example, by asking the patient the clinician finds out that the patient is not suffering from night sweat. For that reason the clinician recategorizes the symptom „might sweat« as absent symptom. Thus, this embodiment allows an iterative process in conducting a differential diagnosis.

According to a further embodiment of the method, a user is enabled to request information entities stored in a record of the patient, the information entities being semantically related to at least one open symptom of said set of likely diseases. For continuing the clinical diagnosis process, clinicians need to find out more information about the open symptoms of the likely diseases. For that reason, this embodiment establishes a request which enables the clinician to discover and highlight any information entities stored in the patient record semantically relating to at least one open symptom of the set of likely diseases. This embodiment of the proposed method relies on data analytics technology and uses information about open symptoms as query request. If the system provides a historical data entry, e.g. a test result two years ago, which is related to the currently requested symptom set, the clinician can decide to change the classification of symptoms accordingly. In addition, as the system highlights the disease-relevant historical information units, the user, or, synonymously, the clinician is indirectly suggested to re-think and re-interpret the relevance and meaning of the open symptoms as well as to avoid the execution of not required, and/or cost-intensive examinations.

According to a further embodiment of the method recommended examination steps are inferred by evaluating existing, absent and/or open symptoms in view of said disease-symptom knowledge model. By incorporating the information about the existing, absent and open systems of each single likely disease, the proposed method is able to infer the most appropriate examination. For inferring recommendation for examinations, the proposed method relies on the information captured within the disease-symptom model and, optionally, a ranking algorithm.

According to a further embodiment of the method the initial symptoms include symptoms which have been excluded or falsified by an examination or by an anamnesis conducted with the patient. These symptoms are also referred to as „negated« symptoms. For example, by asking the patient the clinician finds out that the patient is not suffering from night sweat. For that reason the clinician re-categorizes the symptom „might sweat« as absent symptom.

According to a further embodiment, the method is repeated or recurred on the basis of mapped and categorized associated symptoms. As one will understand, for this recurring step the associated symptoms which have been categorized into disjoint categories by mapping associated symptoms with initial symptoms are again input by treating the associated symptoms as initial symptoms and repeating or recurring the method.

Embodiments of the proposed method supports a rational of a differential diagnosis. Conducting a differential diagnosis, a clinician usually collects an initial set of symptoms by way of an anamnesis. For each symptom being a leading symptom for a particular disease, said disease is labeled as „likely disease« . In the progress of the diagnosis, the clinician aims to either exclude likely diseases from the list, e.g. if other associated leading symptoms are proven as absent, or rank the set of likely diseases. For doing so, additional examinations helping the clinician to learn more about open or absent symptoms, are executed.

Accordingly, embodiments of the method may allow the clinician to efficiently navigate and analyze the available patient data captured with a patient record to access the relevant information required for accomplishing a diagnosis or treatment decision. The patient data may include time series of data sets covering the outcome of previous and current medical, examinations, identified findings, etc.

According to a first step of an example embodiment, a patient p represented as a set of symptoms $S(p)$ with $S(p)$ comprising any type of symptoms, findings, measurement, signs, or clinical observations. The set of symptoms $S(p)$ may further include symptoms which have been excluded or falsified by an examination or by an anamnesis conducted with the patient. These symptoms are also referred to as »negated« symptoms.

In order to distinguish these symptoms determined for the patient from symptoms which will be, in a further step, associated to likely diseases, the former symptoms determined for the patient are designated »initial symptoms« whereas the latter symptoms are designated »associated symptoms«. Thus, the patient p is represented by an initial set of symptoms, for instance the symptoms discovered within the anamnesis examinations. The representation of the patient by a plurality of initial symptoms may include characteristics of the patient, which hereinafter are accordingly subsumed under the term »symptoms«. These characteristics of the patient include the patient's age, the patient's gender, the patient's lifestyle habits, e.g. consumption of alcohol, tobacco products etc.

According to a further step, at least one likely disease for each of the plurality of initial symptoms is determined. The determination is supported by querying and reasoning in a disease-symptom knowledge model. The disease-symptom knowledge model is a formal representation of knowledge about possible relationships between diseases and symptoms. In addition, the disease-symptom knowledge model may be enriched by information about the possible relationships between symptoms and related examination, whereby a proposed examination may be assigned to a symptom for the case that a performance of this examination helps to find out whether a symptom is existent or absent. Further on, each disease d may relate to a set of leading Symptoms LS(d) and a set of possible symptoms PS(d). Expressed formally, for each initial symptom $s \in S(p)_{initial}$ significantly related diseases $D_s$ are identified by querying and reasoning over the disease-symptom model. A disease d is significantly related to a symptom s, if s is leading symptom of d ($s \in LS(d)$). As a result of this step, the patient p is mapped onto a set of likely diseases $D(p)_{likely}$, i.e. onto the union of significantly related diseases $D_s$ for each $s \in S(p)_{initial}$.

According to a further step, for each likely disease a plurality of associated symptoms is determined, the associated symptoms being associated to a respective disease of said set of likely diseases in said disease-symptom knowledge model. Expressed formally, for each disease $d \in D_{likely}$ the set of associated symptoms:

$$AS(d) = \{s(d)1, s(d)2, s(d)3, s(d)4, \ldots\}$$

is identified by querying and reasoning over the disease-symptom model.

According to a further step, each of the plurality of associated symptoms is categorized into disjoint categories by mapping associated symptoms with initial symptoms. The patient data, i.e. the initial set of symptoms $S(p)_{initial}$ of Patient p, is used to classify the set of associated symptoms AS(d) into three disjoint categories:

$$AS(d) \rightarrow AS(d)_{existing} \times AS(d)_{open} \times AS(d)_{absent}$$

with each $x \in AS(d)$ being mapped into exactly one category and with:
- $x \in AS(d)$ is mapped onto the category $AS(d)_{existing}$ if and only if the symptom x belongs to the set of initial symptoms S(p)initial
- $x \in AS(d)$ is mapped onto the category $AS(d)_{absent}$ if and only if there is test result that states that symptom x belongs NOT to the set of initial symptoms S(p)initial
- $x \in AS(d)$ is mapped onto the category $AS(d)_{open}$ else According to a further step, likely diseases are represented in the context of said categories of associated symptoms. In the context of one patient p, the information of likely disease and the associated classification of symptoms are represented to the clinician.

FIG. 1 shows an exemplary user interface for representing likely diseases in the context of said categories of associated symptoms.

A main window in the upper right, which is partially covered by a detail window in the lower right, represents a set of likely diseases »colorectal cancer«, »diverticulitis«, »hodgkin-lymphoma«, »non-hodgkin-lymphoma« and »lymphadenitis«. The symptom information for those diseases is represented by bars.

A respective upper bar assigned to a respective likely disease and captioned LS (»leading symptoms«) represents a coverage of existing, absent and open leading symptoms. A respective lower bar assigned to a respective likely disease and captioned S (»symptoms«) represents a coverage of existing, absent and open symptoms.

The particular symptoms or leading may be displayed by hovering the mouse pointer over the respective bar area, which is shown for open symptoms for the disease »hodgkin-lymphoma«. The list includes open symptoms like night-sweats, alcohol related pain in lymph nodes, enlarged spleen, fever, weight-loss and enlarged mediastinal lymph node. By clicking the mouse pointer on the respective bar area, a detail window is displayed which is shown in the lower right of the drawing.

Within this detail window, the clinician is enabled to change the categories »present« (=existing), »open« and »absent« of each of the plurality of associated symptoms with regard to an examination result.

Figure 2:
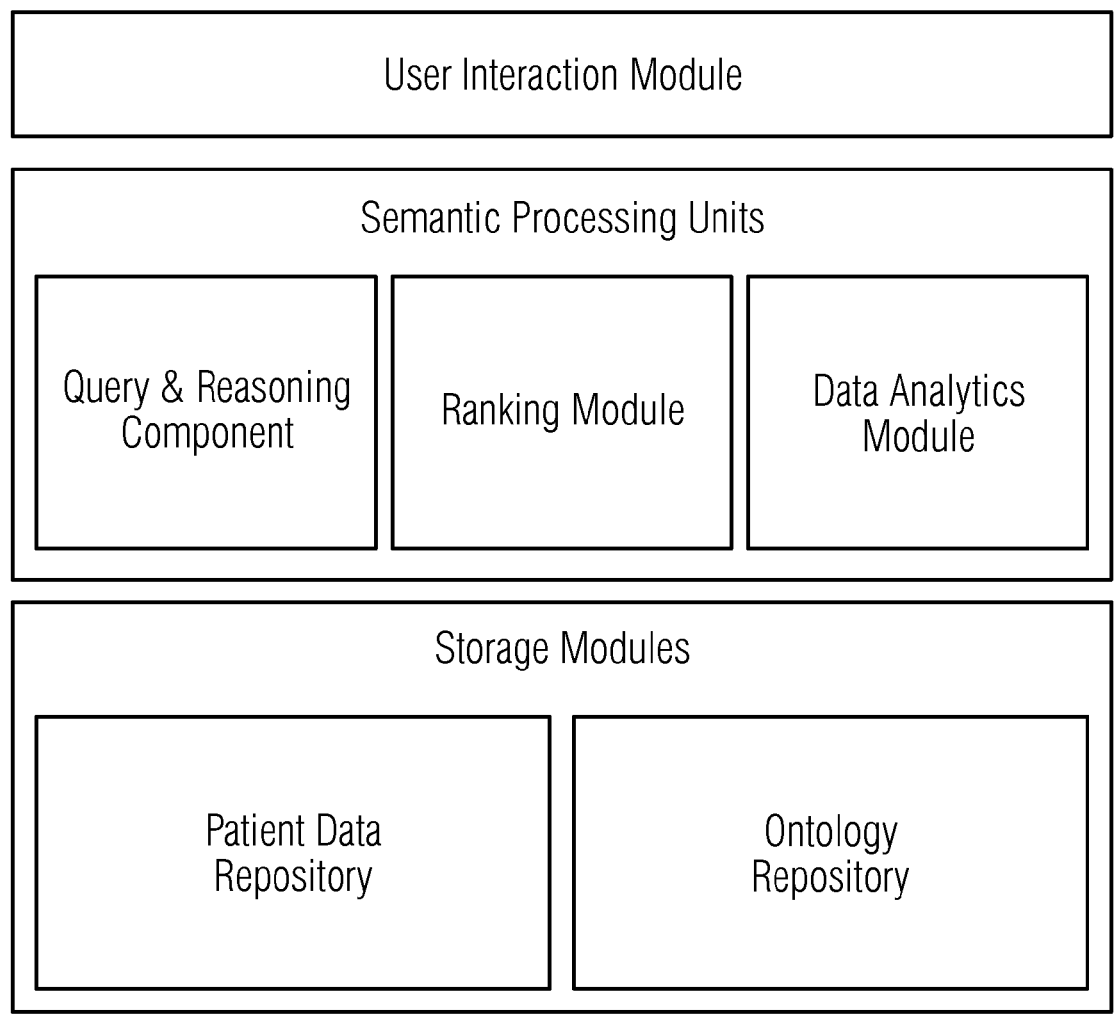
FIG. 2 shows a structural view of functional components of an example system according to one embodiment.

FIG. 2 shows a structural view of functional components of a system according to an embodiment of the proposed idea. The functional components are structured in three layers captioned storage modules, semantic processing units and user interaction module.

Within the storage module layer, a module captioned »Patient Data Repository«, or, patient record is provided. This module is the storage location of the patient data and the associated semantic annotations.

A further module within the storage module layer captioned »Ontology Repository« provides medical ontologies, particularly at least one medical ontology, at least one annotation ontology and at least one disease-symptom model. Medical Ontologies provide standardized labels for the semantic annotations of the information entities of the patient data repository. An Annotation Ontology provides means to store semantic annotations in a structured manner and to efficiently align concept/labels of medical ontologies with information entities of the patient data repository. The disease-symptom model captures the relationship between disease concepts and their leading symptoms as well as their related measurements, findings or observations. The concepts of the disease-symptom model are again semantically aligned with concepts of medical ontologies.

The semantic processing units layer is enabling the seamless integration of patient data, provided ontologies, as well as continuous user input in order to process and provide the most appropriate, requested information to the user.

Within the semantic processing units layer, a module captioned »Query and Reasoning Module« is provided. This module operates on the set of symptoms representing the patient's current condition as well as the medical ontologies, the disease-symptom ontology and the annotation ontology. The query and reasoning module automatically detects the set, or, at least one, likely disease for each of the plurality of initial symptoms of the patient.

Further on, the query and reasoning module automatically classifies, or, categorizes, each of the plurality of associated symptoms into disjoint categories by mapping associated symptoms with initial symptoms in the context of one likely disease. The disjoint categories may be captioned as „open«, „absent«, or „existing«.

According to one embodiment, the query and reasoning module detects relevant examinations which are recommended to the clinician.

According to a further embodiment, a further module within the semantic processing units layer captioned „Ranking Module« allows ranking of requested information according to a predefined ranking-algorithm and ranking metrics incorporation the relevant decision criteria, for instance urgency of the examination, cost of an examination, insurance terms of the patient, etc.

According to a further embodiment, a further module within the semantic processing units layer captioned „Data Analytics Module« allows cleaning, transforming and annotating input data, i.e. query request relating to the set of open symptoms related to a particular likely disease, with the goal of highlighting relevant information entries, such as past examinations related to a likely disease or a open symptom. The data analytics module is processing the historical information entities of the patient record and identifies contained concepts and relations between them using the medical ontologies as well as the disease-symptom model. In other words, the data analytics module automatically accesses and highlights relevant historical examinations in the patient record that help the clinician to learn about the progress or change of measurements, findings and symptoms over time.

The layer „User Interaction module« is operating the representation of likely diseases in the context of said categories of associated symptoms.

According to a further embodiment, the user interaction module additionally enables an efficient navigation within patients' disease, symptoms and finding information.

According to a further embodiment, the user interaction module additionally triggers the system to highlight and display relevant information entities, for instance recommended examinations or related historical test results, and allows the user to access related historical information entities stored on the patient record.

According to a further embodiment, the user interaction module additionally provides means for changing or updating the patient data in the patient record.

The proposed idea discloses a combination and integration of existing semantic technologies paving the way towards efficient representation and management of patient's disease and symptoms information as basis for improved clinical diagnosis.

The proposed idea offers an integration of medical expert knowledge, i.e. the explicit representation of disease-symptom model, to improve the access and navigation within complex and heterogeneous clinical knowledge resources.

The proposed idea uses semantic knowledge processing in order to capture semantic relationships between data entries over time and to infer implicit additional knowledge.

The proposed idea allows for the simultaneous access to past data entry, i.e. the patient's historical examinations, as well as common knowledge, e.g. recommendation in terms of most efficient, future examinations.

The proposed idea relies on data analysis technology in order to detect information about open symptoms in the historical data. Thus the idea implements means allowing the user to actively search for related information assets that help her or him in fine-tuning and refining the current patient data.

By means of a user interaction mechanism a semantic processing of data, e.g. querying and reasoning over data, data analytics and ranking of results, are accomplished while users are providing new information to the systems, and thus, accordingly changed or updated.

Various embodiments can be implemented in computing hardware (computing apparatus) and/or software, including but not limited to any computer or microcomputer that can store, retrieve, process and/or output data and/or communicate with other computers.

The processes can also be distributed via, for example, downloading over a network such as the Internet. A program/software implementing the embodiments may be recorded on computer-readable media comprising computer-readable recording media. The program/software implementing the embodiments may also be transmitted over a transmission communication media such as a carrier wave.

The invention has been described in detail with particular reference to example embodiments thereof, but it will be understood that variations and modifications can be effected within the spirit and scope of the invention covered by the claims.

What is claimed is:

1. A method for supporting a clinical diagnosis, comprising:
   a) receiving, by a processor, semantically annotated initial symptom data for a patient indicating, for each of a plurality of initial symptoms, a determination of whether that initial symptom is present in the patient or absent from the patient;
   b) determining, by the processor, by querying and reasoning in a disease-symptom knowledge model, at least one likely disease for each of the plurality of initial symptoms indicated as present in the patient according to the received initial symptom data;
   c) mapping, by the processor, the plurality of initial symptoms onto a set of said likely diseases;
   d) determining, by the processor, for each disease of said set of likely diseases a plurality of associated symptoms, the associated symptoms being associated to a respective disease of said set of likely diseases in said disease-symptom knowledge model;
   e) for each disease of said set of likely diseases, categorizing, by the processor, each of the plurality of associated symptoms of the respective disease into one of the following disjoint categories by mapping each associated symptom corresponding with the respective disease with the plurality of initial symptoms,
      wherein each associated symptom of the disease that is indicated by the initial symptom data as being present in the patient is categorized as an existing symptom;
      wherein each associated symptom of the disease that is indicated by the initial symptom data as being absent from the patient is categorized as an absent symptom; and
      wherein each associated symptom of the disease that is not indicated by the initial symptom data as being present in or absent from the patient is categorized as an open symptom; and
   f) displaying, at a user interface, likely diseases in the context of said categories of associated symptoms, including displaying, for each likely disease, an indication of whether each associated symptom of that disease has been categorized as an existing symptom, an absent symptom, or an open symptom based on the initial symptom data for the patient.

2. The method of claim 1, including the step of:
g) enabling a user to change said categories of each of the plurality of associated symptoms.

3. The method of claim 2, including the step of:
h) enabling a user to request information entities stored in a record of the patient, the information entities being semantically related to at least one open symptom of said set of likely diseases.

4. The method of claim 3, including the step of:
i) inferring recommended examination steps by evaluating existing, absent and/or open symptoms in view of said disease-symptom knowledge model.

5. The method of claim 1, wherein said initial symptoms include at least one of findings, observations, symptoms, and negated symptoms.

6. The method of claim 1, including the step of:
treating the associated symptoms in step e) as initial symptoms and recurring the steps b) until f).

7. A system for supporting a clinical diagnosis, the system comprising:
a semantic patient database stored in non-transitory computer-readable media and including semantically annotated initial symptom data for a patient indicating, for each of a plurality of initial symptoms, a determination of whether that initial symptom is present in the patient or absent from the patient;
an ontology database stored in non-transitory computer-readable media and including a knowledge model establishing a relationship between a plurality of diseases and a plurality of associated symptoms for each respective disease; and
at least one processor having access to the semantic patient database and the ontology database and configured to execute computer-readable instructions to:
map the plurality of initial symptoms onto a set of likely diseases and for mapping the plurality of initial symptoms onto a set of said likely diseases;
for each disease of said set of likely diseases, categorize each of the plurality of associated symptoms of the respective disease into disjoint categories by mapping each associated symptom corresponding with the respective disease with the plurality of initial symptoms,
wherein each associated symptom of the disease that is indicated by the initial symptom data as being present in the patient is categorized as an existing symptom;
wherein each associated symptom of the disease that is indicated by the initial symptom data as being absent from the patient is categorized as an absent symptom; and
wherein each associated symptom of the disease that is not indicated by the initial symptom data as being present in or absent from the patient is categorized as an open symptom; and
cause the display of likely diseases in the context of said categories of associated symptoms, including displaying, for each likely disease, an indication of whether each associated symptom of that disease has been categorized as an existing symptom, an absent symptom, or an open symptom based on the initial symptom data for the patient.

8. The system of claim 7, wherein the at least one processor are further configured to enable a user to change said categories of each of the plurality of associated symptoms.

9. The system of claim 7, wherein the at least one processor are further configured to enable a user to request information entities stored in a record of the patient, the information entities being semantically related to at least one open symptom of said set of likely diseases.

10. The system of claim 7, wherein said initial symptoms include at least one of findings, observations, symptoms, and negated symptoms.

11. A computer program product, which comprises a non-transitory computer-readable medium storing a program code which, when executed by a processor, is configured to:
a) receive semantically annotated initial symptom data for a patient indicating, for each of a plurality of initial symptoms, a determination of whether that initial symptom is present in the patient or absent from the patient;
b) determine, by querying and reasoning in a disease-symptom knowledge model, at least one likely disease for each of the plurality of initial symptoms indicated as present in the patient according to the received initial symptom data;
c) map the plurality of initial symptoms onto a set of said likely diseases;
d) determine for each disease of said set of likely diseases a plurality of associated symptoms, the associated symptoms being associated to a respective disease of said set of likely diseases in said disease-symptom knowledge model;
e) for each disease of said set of likely diseases, categorizing each of the plurality of associated symptoms of the respective disease into disjoint categories by mapping each associated symptom corresponding with the respective disease with the plurality of initial symptoms,
wherein each associated symptom of the disease that is indicated by the initial symptom data as being present in the patient is categorized as an existing symptom;
wherein each associated symptom of the disease that is indicated by the initial symptom data as being absent from the patient is categorized as an absent symptom; and
wherein each associated symptom of the disease that is not indicated by the initial symptom data as being present in or absent from the patient is categorized as an open symptom; and
f) display likely diseases in the context of said categories of associated symptoms, including displaying, for each likely disease, an indication of whether each associated symptom of that disease has been categorized as an existing symptom, an absent symptom, or an open symptom based on the initial symptom data for the patient.

* * * * *